(12) United States Patent
Kasai et al.

(10) Patent No.: US 10,168,208 B2
(45) Date of Patent: Jan. 1, 2019

(54) LIGHT AMOUNT DETECTION DEVICE, IMMUNE ANALYZING APPARATUS AND CHARGED PARTICLE BEAM APPARATUS THAT EACH USE THE LIGHT AMOUNT DETECTION DEVICE

(71) Applicant: HITACHI HIGH-TECHNOLOGIES CORPORATION, Tokyo (JP)

(72) Inventors: Yutaka Kasai, Tokyo (JP); Fujio Onishi, Tokyo (JP); Osamu Tasaki, Tokyo (JP); Hidetsugu Tanoue, Tokyo (JP); Kazuhiro Tanaka, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/561,190

(22) PCT Filed: Mar. 16, 2016

(86) PCT No.: PCT/JP2016/058339
§ 371 (c)(1),
(2) Date: Sep. 25, 2017

(87) PCT Pub. No.: WO2016/158421
PCT Pub. Date: Oct. 6, 2016

(65) Prior Publication Data
US 2018/0066986 A1    Mar. 8, 2018

(30) Foreign Application Priority Data
Apr. 3, 2015    (JP) .................................. 2015-077060

(51) Int. Cl.
*G01J 1/44*    (2006.01)
*G01T 1/28*    (2006.01)
(Continued)

(52) U.S. Cl.
CPC . *G01J 1/44* (2013.01); *G01J 1/42* (2013.01); *G01N 21/66* (2013.01); *G01N 21/956* (2013.01);
(Continued)

(58) Field of Classification Search
CPC .... G01J 1/44; G01N 21/66; H01J 1/32; G01T 1/28
See application file for complete search history.

(56) References Cited

U.S. PATENT DOCUMENTS

| 5,663,564 A | 9/1997 | Radford |
| 2006/0028563 A1 | 2/2006 | Tomaney et al. |

(Continued)

FOREIGN PATENT DOCUMENTS

| JP | 2001-141560 A | 5/2001 |
| JP | 2008-509399 A | 3/2008 |

(Continued)

OTHER PUBLICATIONS

International Preliminary Report on Patentability received in corresponding International Application No. PCT/JP2016/058339 dated Oct. 12, 2017.

(Continued)

*Primary Examiner* — Casey Bryant
(74) *Attorney, Agent, or Firm* — Mattingly & Malur, PC

(57) ABSTRACT

A signal detected by a photomultiplier tube is pre-amplified and converted into a digital signal. A time average value of signal components, each of which has a voltage lower than a predetermined base threshold value, is calculated as a base voltage. A signal that has been subjected to base correction processing is subjected to threshold value processing and to base correction processing in a non-incident state in which light is not incident on the photomultiplier tube. An output signal thereof is subjected to dark current calculation pro- (Continued)

cessing; and a light emission signal amount is calculated by subtracting, from the signal component of the detection light obtained by the threshold value processing, a time average value of the signal components of the dark current. As the result, discriminating the dark current pulse from floor noises enhances the accuracy of the base voltage, and thus the accuracy of light detection.

7 Claims, 6 Drawing Sheets

(51) Int. Cl.
| | |
|---|---|
| *G01N 23/20* | (2018.01) |
| *G01N 23/203* | (2006.01) |
| *G01N 23/22* | (2018.01) |
| *G01N 23/225* | (2018.01) |
| *G01J 1/42* | (2006.01) |
| *G01N 21/66* | (2006.01) |
| *G01N 21/956* | (2006.01) |
| *G01T 1/164* | (2006.01) |
| *G01T 1/20* | (2006.01) |

(52) U.S. Cl.
CPC .......... *G01N 23/203* (2013.01); *G01N 23/22* (2013.01); *G01N 23/225* (2013.01); *G01T 1/1647* (2013.01); *G01T 1/20* (2013.01)

(56) References Cited

U.S. PATENT DOCUMENTS

| | | |
|---|---|---|
| 2011/0127415 A1 | 6/2011 | Kanter |
| 2013/0114073 A1 | 5/2013 | Namba et al. |
| 2014/0332668 A1 | 11/2014 | Nishihara et al. |
| 2015/0153223 A1 | 6/2015 | Onishi et al. |
| 2015/0364635 A1 | 12/2015 | Bodlovic et al. |

FOREIGN PATENT DOCUMENTS

| | | |
|---|---|---|
| JP | 2008-256380 A | 10/2008 |
| JP | 2013-187511 A | 9/2013 |
| WO | 2012/017762 A1 | 2/2012 |
| WO | 2013/084839 A1 | 6/2013 |
| WO | 2013/187511 A1 | 12/2013 |
| WO | 2014/118537 A1 | 8/2014 |

OTHER PUBLICATIONS

International Search Report of PCT/JP2016/058339 dated Jun. 7, 2016.

LIGHT AMOUNT DETECTION DEVICE, IMMUNE ANALYZING APPARATUS AND CHARGED PARTICLE BEAM APPARATUS THAT EACH USE THE LIGHT AMOUNT DETECTION DEVICE

TECHNICAL FIELD

The present invention relates to a light amount detection device that detects light to measure a light amount, and to an immune analyzing apparatus and a charged particle beam apparatus that each use the light amount detection device.

BACKGROUND ART

Photomultiplier tubes are each capable of taking out very weak light as an electric signal, and therefore are used in various kinds of fields. For example, a photometer irradiates a sample with light to detect fluorescence generated from the sample by using a photomultiplier tube, and analyzes very small amounts of components contained in the sample. In addition, a charged particle beam apparatus irradiates a sample with an electron beam, converts a weak secondary electron generated from a surface of the sample into light by using a scintillator, and detects the light by using a photomultiplier tube to minutely observe the surface of the sample.

As a technique related to the detection of light by using such a photomultiplier tube, for example, PTL 1 (International Publication No. 2013/187511) discloses a technique related to an optical signal detection circuit provided with: amplification means for amplifying an analogue detection signal according to a light amount detected by light detection means; analog to digital conversion means for converting the analogue detection signal amplified by the amplification means into a digital detection signal; threshold value determination means for detecting a pulse from the digital detection signal converted by the analog to digital conversion means, and repeating processing of detecting the energy of the detected pulse to determine the frequency of appearance of pulses on a detected energy basis, thereby determining a pulse determination threshold value on the basis of the determined frequency of appearance of pulses on an energy basis; and threshold-value processing means for outputting, as a detection signal, the digital detection signal containing a pulse, the energy of which is higher than or equal to the pulse determination threshold value determined by the threshold value determination means.

CITATION LIST

Patent Literature

PTL 1: International Publication No. 2013/187511

SUMMARY OF INVENTION

Technical Problem

In recent years, photometers and charged particle beam apparatuses require still higher accuracy, and need to detect a still smaller amount of light.

However, in the above-described prior art, although a threshold value is determined to discriminate a signal component of light from signal components of noises originating from a dark current, discrimination between the signal components of noises originating from the dark current and signal components of floor noises is not taken into consideration, and consequently a correct base voltage cannot be determined. Therefore, there arises a problem that it is not possible to correctly acquire a value of a signal component of light, the value being determined by a comparison with this base voltage.

The present invention has been made taking the above-described problem into consideration, and an object of the present invention is to provide a light amount detection device that discriminates a dark current pulse from floor noises, thereby enabling to enhance the accuracy of a base voltage, and to enhance the accuracy of light detection, and to provide an immune analyzing apparatus and a charged particle beam apparatus that each use the light amount detection device.

Solution to Problem

In order to achieve the above-described object, the present invention provides a light amount detection device including: an amplifier that performs amplification processing of amplifying a detection signal from a light detection unit for detecting light; an A/D converter that performs A/D conversion processing of converting the detection signal amplified by the amplifier into a digital signal to output the digital signal; a base voltage calculation part that performs base voltage calculation processing of, for the output signal from the A/D converter, calculating, as a base voltage, a time average value of signal components each having a voltage lower than a predetermined base threshold value; a base correction processing part that performs base correction processing of offsetting the output signal from the A/D converter in such a manner that the base voltage calculated by the base voltage calculation part becomes 0; a dark current calculation part that performs dark current calculation processing of, for an output signal from the base voltage calculation processing part in a non-input state in which light is not input into the light detection unit, calculating, as a dark current pulse, a signal component having a voltage higher than a predetermined signal detection threshold value; a threshold value processing part that performs threshold value processing of, for the output signal from the base voltage calculation processing part, calculating, as a detection light pulse, a signal component having a voltage higher than a predetermined signal detection threshold value; and a light emission signal amount calculation part that performs light emission signal amount calculation processing of calculating a light emission signal amount by subtracting, from the signal component of the detection light obtained by the threshold value processing, a time average value of the signal components of the dark current obtained by the dark current calculation processing.

Advantageous Effects of Invention

Discriminating a dark current pulse from floor noises enables to enhance the accuracy of the base voltage, and thus to enhance the accuracy of light detection.

DESCRIPTION OF EMBODIMENTS

Embodiments of the present invention will be described with reference to drawings.

First Embodiment

A first embodiment of the present invention will be described with reference to FIGS. 1 to 6.

Figure 1:
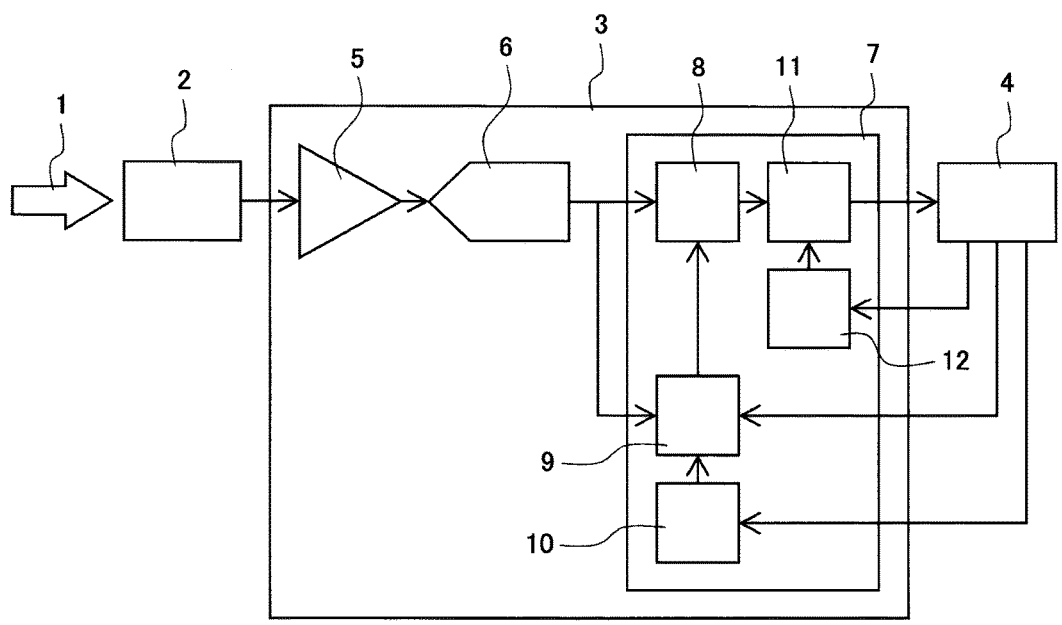
FIG. 1 is a diagram schematically illustrating an overall configuration of a light amount detection device according to a first embodiment.

FIG. 1 is a diagram schematically illustrating an overall configuration of a light amount detection device according to the present embodiment.

In FIG. 1, a light amount detection device 100 is schematically configured to include: a photomultiplier tube 2 as a light detection unit that detects incident light to convert the incident light into a current, and outputs the current as a detection signal; a preamplifier 5 as an amplifier that performs amplification processing of amplifying the detection signal from the photomultiplier tube 2; an A/D converter 6 that performs A/D conversion processing of converting the detection signal amplified by the preamplifier 5 into a digital signal to output the digital signal; a base voltage calculation part 9 that performs base voltage calculation processing of, for an output signal from the A/D converter 6, calculating, as a base voltage, a time average value of signal components each having a voltage lower than a predetermined base threshold value; a base threshold value input part 10 that inputs a base threshold value into the base voltage calculation part 9 on the basis of an instruction from a computer (PC) 4; a base correction processing part 8 that performs base correction processing of offsetting an output signal from the A/D converter 6 in such a manner that the base voltage calculated by the base voltage calculation part 9 becomes 0 (zero); a threshold value processing part 11 as a dark current calculation part that performs threshold value processing of, for an output signal from the base correction processing part 8, calculating, as a detection light pulse, a signal component having a voltage higher than a predetermined signal detection threshold value, and dark current calculation processing of, for an output signal from the base correction processing part 8 in a non-incident state in which light is not incident on the photomultiplier tube 2, calculating, as a dark current pulse, a signal component having a voltage higher than a predetermined signal detection threshold value; a signal detection threshold value input part 12 that inputs a signal detection threshold value into the threshold value processing part 11 on the basis of an instruction from the PC 4; and a PC 4 as a light emission signal amount calculation part that performs light emission signal amount calculation processing of calculating a light emission signal amount by subtracting, from the signal component of the detection light obtained by the threshold value processing, a time average value of the signal components of the dark current obtained by the dark current calculation processing.

The base correction processing part 8, the base voltage calculation part 9, the base threshold value input part 10, the threshold value processing part 11, and the signal detection threshold value input part 12 are configured on, for example, a FPGA (Field Programmable Gate Array) as an operation unit 7 that subjects the digital signal input from the A/D converter 6 to operation processing so as to enhance SNR of the amount of measured signal. In addition, the preamplifier 5, the A/D converter 6, and the operation unit 7 constitute the detection circuit 3 that handles a signal from the photomultiplier tube 2 to transmit the signal to the PC 4 as an overall control unit that controls the operation of the light amount detection device 100 as a whole.

The photomultiplier tube 2 outputs a current according to the light amount of detection target light (detection light) 1. However, even in a state in which detection light 1 is not input, a dark current generated by a thermal cause or the like is output to the preamplifier 5 at a constant probability.

The preamplifier 5 is configured to include an operational amplifier, a feedback resistance for current-voltage conversion, a capacitor for frequency band setting, and a differential amplifier circuit, (all of which are not illustrated). The preamplifier 5 converts an output signal (output current) from the photomultiplier tube 2 into a voltage signal, and then inputs the voltage signal into the A/D converter 6.

The A/D converter 6 converts the voltage signal inputted from the preamplifier 5 into digital data. The A/D converter 6 has only to have a resolution capable of resolving a minute voltage. The A/D converter 6 to be used has a resolution, for example, at a level at which a sampling time interval is 4 μs, and a voltage resolution is 0.6 μV.

The PC 4 controls the operation of the light amount detection device 100 as a whole, inputs parameters into the base voltage calculation part 9, the base threshold value input part 10, and the signal detection threshold value input part 12, and instructs starting and stopping of light amount detection processing in the light amount detection device 100. In addition, the PC 4 accumulates data input from the detection circuit 3, and performs calculation processing, for example, determination of the signal area within a fixed period of time.

Figure 2:
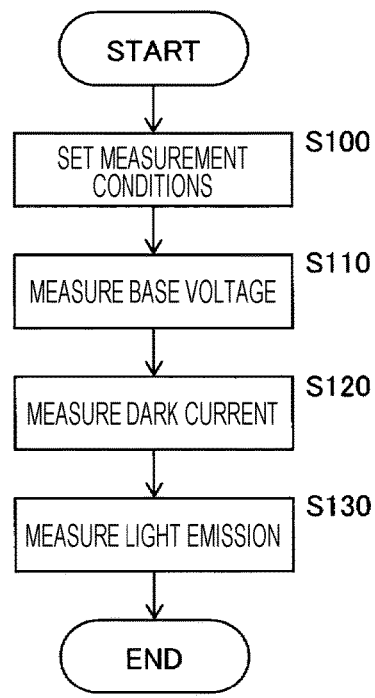
FIG. 2 is a flowchart illustrating processing of detecting detection light in the light amount detection device according to the first embodiment.

FIG. 2 is a flowchart illustrating processing of detecting detection light in the light amount detection device.

In the detection processing shown in FIG. 2, first of all, the PC 4 sets parameters (including a base threshold value) in the base threshold value input part 10, and sets parameters (including a signal detection threshold value) in the signal detection threshold value input part 12. Subsequently, the PC 4 instructs the detection circuit 3 to start base voltage calculation processing (step S100).

When the base voltage calculation processing is instructed, the base voltage calculation part 9 calculates a base voltage on the basis of the parameters set by the PC 4 (step S110). The base voltage calculation processing is repeatedly performed until an instruction to stop the base voltage calculation processing is made by the PC 4.

After a base voltage value is calculated, when the PC 4 starts accumulating output data of the detection circuit 3, dark current calculation processing is started (step S120). In the dark current calculation processing, a signal amount of output signal (dark current) output from the photomultiplier tube 2 is measured in a state in which the detection light 1 is not incident on the photomultiplier tube 2.

Next, incident light of the detection light 1 on the photomultiplier tube 2 is started, and the signal amount is measured by data processing similar to that in the step S120 (step S130). As the result of the data processing in the PC 4, the real light emission signal amount is output by subtracting a signal equivalent to a dark current from the signal amount at the time of light emission.

Here, each processing of the light amount detection device 100 configured as above will be described in detail.

(1) Base Voltage Calculation Processing

Figure 3:
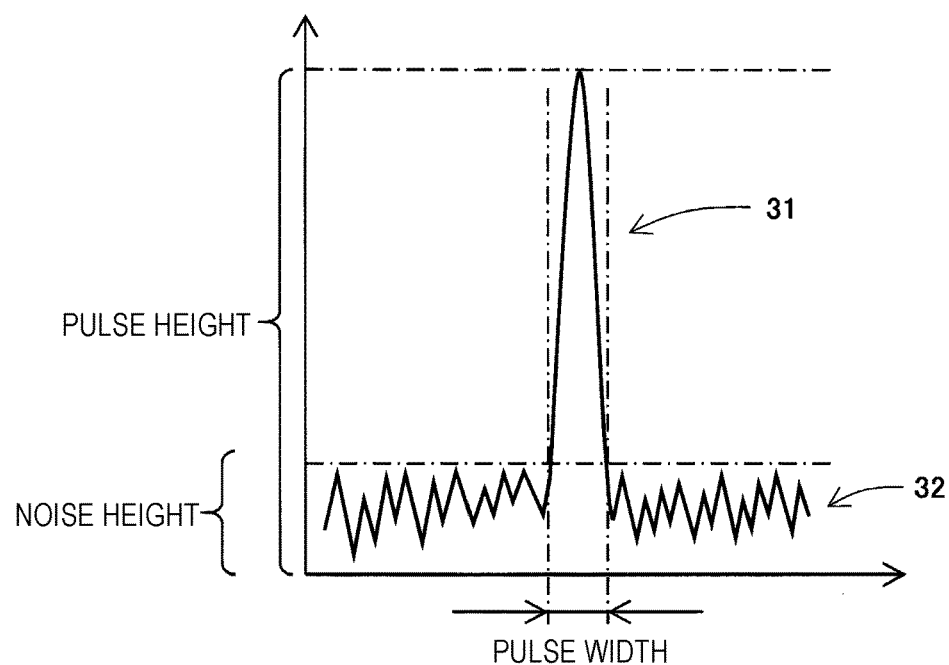
FIG. 3 is a drawing schematically illustrating an output waveform of a dark current pulse in an output of an A/D converter according to the first embodiment.

FIG. 3 is a drawing schematically illustrating an output waveform of a dark current pulse in the output of the A/D converter 6 according to the present embodiment.

In the present embodiment, a gain and a band are adjusted by properly setting a circuit constant of the preamplifier 5, and the band is set at a high-frequency band of 10 kHz in such a manner that an output waveform of the A/D converter 6 gets to a level at which the maximum pulse height is 400 counts, and the pulse width is 25 points, per dark current pulse as indicated in the waveform of FIG. 3. A signal-to-noise ratio at the time when the pulse height is 400 counts and when the noise height is 20 counts is 20, which is high. Thus, a dark current pulse 31 protrudes from noises 32. As the result, the discrimination between the dark current pulse and the noises in the threshold value processing becomes easy.

It should be noted that the count which is a unit of pulse height, and the point which is a unit of pulse width, are normalized by using appropriate values (for example, 1 count=0.6 µV, 1 point=4 µs). The description hereinafter will be made by using similar definitions unless otherwise particularly specified.

Figure 4:
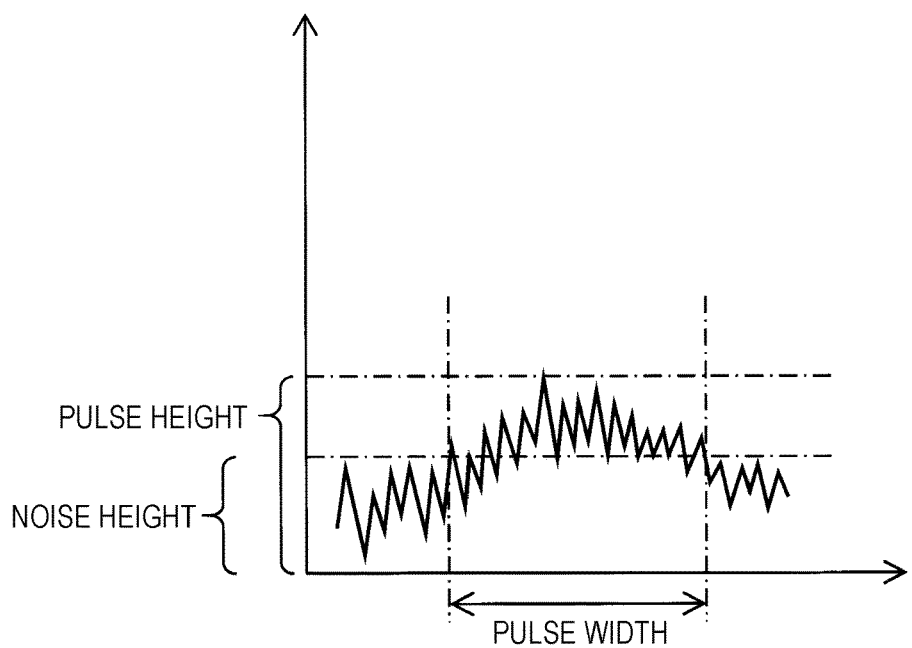
FIG. 4 is a drawing schematically illustrating an output waveform of a dark current pulse as a comparative example of the first embodiment.

FIG. 4 is a drawing schematically illustrating an output waveform of a dark current pulse as a comparative example of the present embodiment.

A comparative example shown in FIG. 4 illustrates a waveform of a dark current pulse obtained when a frequency band of the preamplifier is set at a low-frequency band of 1 kHz. In this case, output data of the A/D converter 6 is at a level at which the maximum pulse height is 40 counts, and the pulse width is 250 points, per dark current pulse. A signal-to-noise ratio at the time when the pulse height is 40 counts and when the noise height is 20 counts is 2, which is low. Thus, the dark current pulse is buried in noises. In such a case, the accuracy in discrimination between the dark current pulse and the noises in the threshold value processing decreases in comparison with that in the present embodiment.

Figure 5:
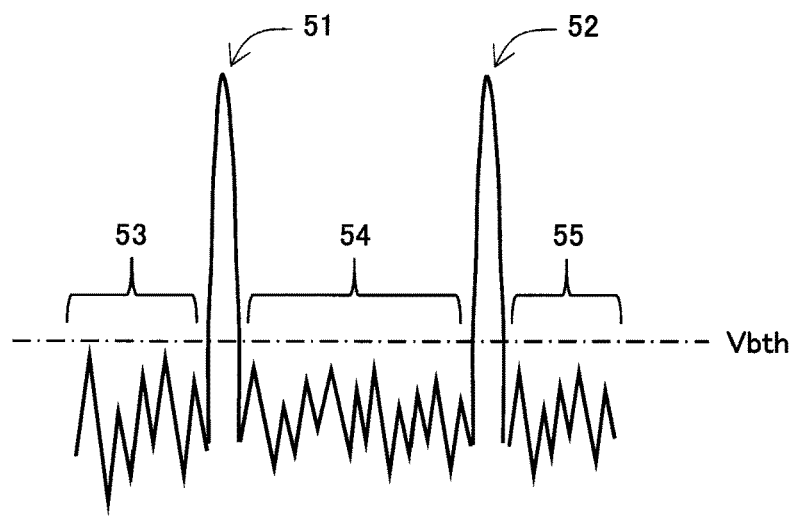
FIG. 5 is a drawing illustrating base voltage calculation processing in a base voltage calculation part according to the first embodiment.

FIG. 5 is a diagram illustrating base voltage calculation processing in the base voltage calculation part.

As shown in FIG. 5, data input into the base voltage calculation part 9 is compared with a set value of a base threshold value Vbth input from the base threshold value input part 10 on a sampling basis, and data that exceeds the base threshold value Vbth, and data that is lower than or equal to the base threshold value Vbth, are separately stored in the base voltage calculation part 9.

In other words, waveform parts 51, 52 of the dark current pulse are stored as data that exceeds the base threshold value Vbth, and floor noise parts 53, 54, 55 are stored as data that is lower than or equal to the base threshold value Vbth. In addition, the sum total of data that is lower than or equal to the base threshold value Vbth is divided by the number of counts as the number of data, thereby calculating an average value, that is to say, a base voltage.

For example, when the calculation time in the base voltage calculation processing is set as within 1000-point sampling, 10000 (=400 counts (pulse height)×25 points (pulse width)) as the signal amount is included in the average value in a situation in which one dark current pulse is included. Therefore, even averaging by 1000 points as the calculation time results in a base voltage error of 10 counts. Not including the pulse waveform parts exhibits an effect of removing this error.

In addition, in order to obtain a more correct base voltage, it is necessary to make a base threshold value as low as possible so as to reduce a dark current signal component contained. However, in the present embodiment, the band of the preamplifier 5 is adjusted to increase the signal-to-noise ratio, and therefore a dark current pulse component is not contained at the time of the calculation of the base voltage. In other words, as with the above-described comparative example, at the time of a low-frequency band of 1 kHz, 750 points, which is obtained by subtracting 250 points as the pulse width from 1000 points as the calculation time, is averaged to determine a base voltage value. However, in the present embodiment, at the time of a high-frequency band of 10 kHz, 975 points, which is obtained by subtracting 25 points as the pulse width from 1000 points as the calculation time, is averaged to determine a base voltage. Thus, the number of points that can be averaged increases, and therefore a more correct base voltage can be calculated.

(2) Base Correction Processing

In the base correction processing in the base correction processing part 8, an output signal from the A/D converter 6 is offset in such a manner that the base voltage calculated by the base voltage calculation part 9 becomes 0 (zero). In other words, the whole output signal from the A/D converter 6 is offset in such a manner that an average value of floor noises consequently becomes 0 (zero).

(3) Threshold Value Processing, Dark Current Calculation Processing

Figure 6:
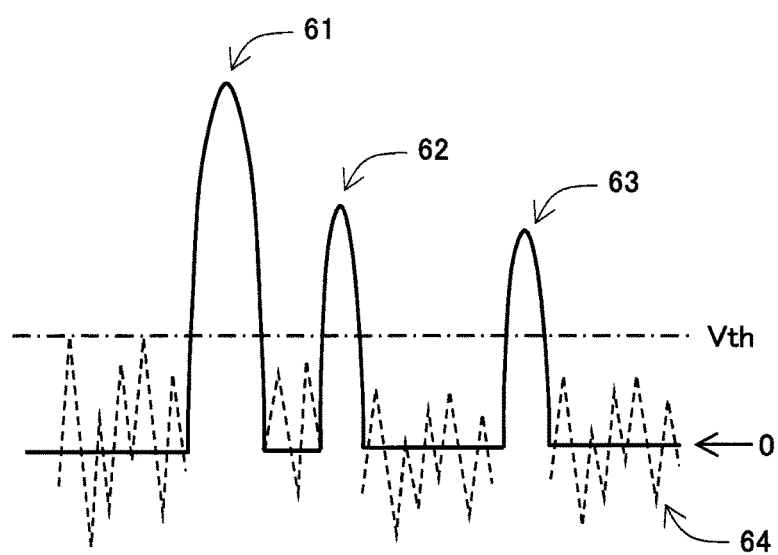
FIG. 6 is a drawing illustrating threshold value processing in a threshold value processing part according to the first embodiment.

FIG. 6 is a drawing illustrating threshold value processing in the threshold value processing part.

As shown in FIG. 6, a signal input into the threshold value processing part 11 from the base correction processing part 8 is compared with a set value of a signal detection threshold value Vth input from the signal detection threshold value input part 12 on a sampling basis, and data that exceeds the signal detection threshold value Vth and data that is lower than or equal to the signal detection threshold value Vth are discriminated.

As with the floor noises 54, data that is lower than or equal to the signal detection threshold value Vth is replaced with 0 (zero), and data of the pulse (the dark current pulse, the detection light pulse) that exceeds the signal detection threshold value Vth is output to the PC 4 as it is.

Incidentally, in the dark current calculation processing, similar processing is performed in a non-incident state in which light is not incident on the photomultiplier tube 2. In addition, when the dark current is calculated, unexpected weak light such as stray light, which differs from the light emission signal as the detection target, may be concurrently measured. However, in the present invention, when the dark current is measured, a calculation may be made with the unexpected weak light included.

In the threshold value processing part 11, with respect to data after the threshold value processing, the base voltage is offset to 0 (zero), and data that is lower than or equal to the signal detection threshold value Vth is then replaced with 0, as indicated in the waveform of FIG. 6. This results in data in a state in which only a photon pulse remains. Therefore, the final signal amount can be output by adding up the number of samplings within the signal amount calculation time.

(4) Light Emission Signal Amount Calculation Processing

In the light emission signal amount calculation processing in the PC 4, the real light emission signal amount of the detection light 1 is output by subtracting a signal equivalent to the dark current obtained by the dark current calculation processing from the signal amount at the time of light emission in a state in which the detection light 1 is incident on the photomultiplier tube 2.

The operation and effects of the present embodiment configured as above will be described.

In the prior art, although a threshold value is determined to discriminate a signal component of light from signal components of noises originating from a dark current, discrimination between the signal components of noises originating from the dark current and signal components of floor noises is not taken into consideration, and consequently a correct base voltage cannot be determined. Therefore, there arises a problem that it is not possible to correctly acquire a value of a signal component of light, the value being determined by a comparison with this base voltage.

Meanwhile, in the present embodiment, the light amount detection device is configured to include: the photomultiplier tube 2 as a light detection unit that detects incident light to convert the incident light into a current, and outputs the current as a detection signal; the preamplifier 5 as an amplifier that performs amplification processing of amplifying the detection signal from the photomultiplier tube 2; the A/D converter 6 that performs A/D conversion processing of converting the detection signal amplified by the preamplifier 5 into a digital signal to output the digital signal; the base voltage calculation part 9 that performs base voltage calculation processing of, for an output signal from the A/D converter 6, calculating, as a base voltage, a time average value of signal components each having a voltage lower than a predetermined base threshold value; the base threshold value input part 10 that inputs a base threshold value into the base voltage calculation part 9 on the basis of an instruction from the PC 4; the base correction processing part 8 that performs base correction processing of offsetting an output signal from the A/D converter 6 in such a manner that the base voltage calculated by the base voltage calculation part 9 becomes 0 (zero); the threshold value processing part 11 as a dark current calculation part that performs threshold value processing of, for an output signal from the base correction processing part 8, calculating, as a detection light pulse, a signal component having a voltage higher than a predetermined signal detection threshold value, and dark current calculation processing of, for an output signal from the base correction processing part 8 in a non-incident state in which light is not incident on the photomultiplier tube 2, calculating, as a dark current pulse, a signal component having a voltage higher than a predetermined signal detection threshold value; the signal detection threshold value input part 12 that inputs a signal detection threshold value into the threshold value processing part 11 on the basis of an instruction from the PC 4; and the PC 4 as a light emission signal amount calculation part that performs light emission signal amount calculation processing of calculating a light emission signal amount by subtracting, from the signal component of the detection light obtained by the threshold value processing, a time average value of the signal components of the dark current obtained by the dark current calculation processing. Therefore, discriminating the dark current pulse from floor noises enables to enhance the accuracy of the base voltage, and thus to enhance the accuracy of light detection.

Modified Example of the First Embodiment

A modified example of the first embodiment according to the present invention will be described.

In the first embodiment, the light amount detection device is configured in such a manner that the operation unit 7 and the PC 4 successively perform each processing for the output signal from the A/D converter 6. However, the present invention is not limited to this configuration. The light amount detection device may be configured in such a manner that the output signal from the A/D converter 6 is stored, and after the acquisition of a required amount of data is completed, the dark current calculation processing and the threshold value processing are performed by using the data.

In this case as well, effects similar to those in the first embodiment can be achieved.

Second Embodiment

A second embodiment of the present invention will be described with reference to FIGS. 7 and 8.

Figure 7:
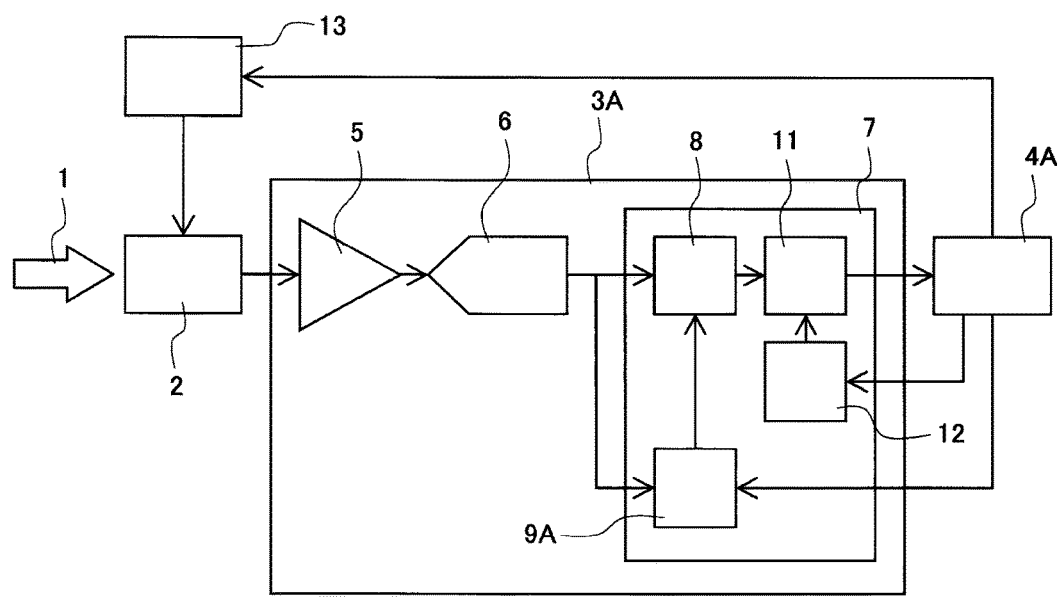
FIG. 7 is a diagram schematically illustrating an overall configuration of a light amount detection device according to a second embodiment.

FIG. 7 is a diagram schematically illustrating an overall configuration of a light amount detection device according to the present embodiment. In the figure, the same reference numerals are used to denote members similar to those in the first embodiment, and thus the description thereof will be omitted.

In FIG. 7, the light amount detection device 100 is schematically configured to include: the photomultiplier tube 2 as a light detection unit that detects incident light to convert the incident light into a current, and outputs the current as a detection signal; the preamplifier 5 as an amplifier that performs amplification processing of amplifying the detection signal from the photomultiplier tube 2; the A/D converter 6 that performs A/D conversion processing of converting the detection signal amplified by the preamplifier 5 into a digital signal to output the digital signal; a base voltage calculation part 9A that performs base voltage calculation processing of calculating a time average value of signal components (noise floor) as a base voltage in a state in which power supply to the photomultiplier tube 2 is interrupted; the base correction processing part 8 that performs base correction processing of offsetting an output signal from the A/D converter 6 in such a manner that the base voltage calculated by the base voltage calculation part 9A becomes 0 (zero); the threshold value processing part 11 as a dark current calculation part that performs threshold value processing of, for an output signal from the base correction processing part 8, calculating, as a detection light pulse, a signal component having a voltage higher than a predetermined signal detection threshold value, and dark current calculation processing of, for an output signal from the base correction processing part 8 in a non-incident state in which detection light is not incident on the photomultiplier tube 2, calculating, as a dark current pulse, a signal component having a voltage higher than a predetermined signal detection threshold value; the signal detection threshold value input part 12 that inputs a signal detection threshold value into the threshold value processing part 11 on the basis of an instruction from a PC 4A; the PC 4A as a light emission signal amount calculation part that performs light emission signal amount calculation processing of calculating a light emission signal amount by subtracting, from the signal component of the detection light obtained by the threshold value processing, a time average value of the signal components of the dark current obtained by the dark current calculation processing; and a detection signal switching unit 13 that switches ON/OFF the operation of the photomultiplier tube 2 on the basis of an instruction from the PC 4A.

The detection signal switching unit 13 switches between supply and interruption of the operating power to the photomultiplier tube 2, thereby switching between presence and absence of the output of a detection signal output from the photomultiplier tube 2 to the A/D converter 6.

The base correction processing part 8, the base voltage calculation part 9A, the threshold value processing part 11, and the signal detection threshold value input part 12 are configured on, for example, a FPGA (Field Programmable Gate Array) as an operation unit 7A that subjects the digital signal input from the A/D converter 6 to operation processing so as to enhance SNR of the amount of measured signal. In addition, the preamplifier 5, the A/D converter 6, and the operation unit 7A constitute the detection circuit 3A that handles a signal from the photomultiplier tube 2 to transmit the signal to the PC 4A as an overall control unit that controls the operation of the light amount detection device 100 as a whole.

Figure 8:
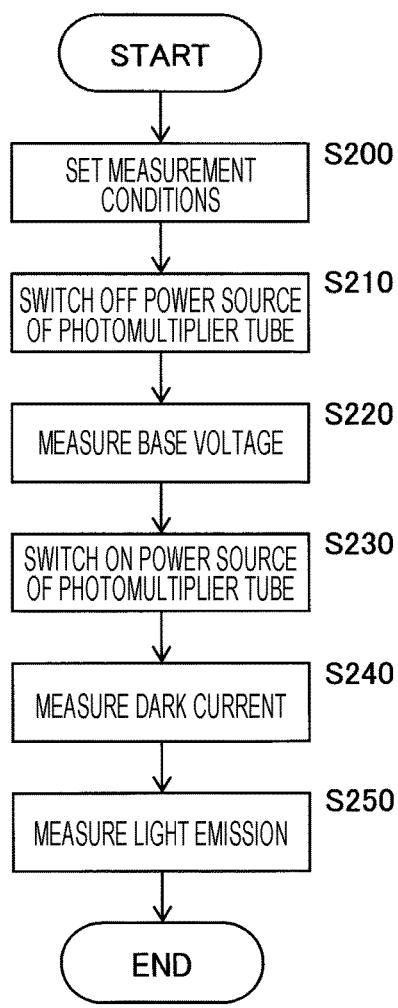
FIG. 8 is a flowchart illustrating processing of detecting detection light in the light amount detection device according to the second embodiment.

FIG. 8 is a flowchart illustrating processing of detecting detection light in the light amount detection device.

In the detection processing shown in FIG. 8, first of all, the PC 4 sets the base measurement time and the signal measurement time (step S200). At this point of time, the photomultiplier tube 2 is in an on state.

Subsequently, the PC 4A inputs, into the detection signal switching unit 13, an instruction to turn off the power supply to the photomultiplier tube 2 (step S210).

Subsequently, when the power supply to the photomultiplier tube 2 is stopped, the PC 4A accumulates output data of the A/D converter 6, and calculates an average value within the base measurement time (step S220). At this point of time, the photomultiplier tube 2 is in a stopped state. Accordingly, a dark current pulse is not generated, and therefore digital data contains only floor noises of the preamplifier 5 at the time of no input. Consequently, the base voltage value obtained by averaging does not contain an error factor caused by a dark current.

Subsequently, the PC 4A outputs, to the detection signal switching unit 13, an instruction to supply the power to the photomultiplier tube 2 (step S230). Incidentally, the output current of the photomultiplier tube 2 largely depends on a stable state of a power supply source, and therefore the PC 4A waits until the supply power to the photomultiplier tube 2 is sufficiently stabilized.

Subsequently, the PC 4A measures, within a fixed period of time, a dark current of the photomultiplier tube 2 in a non-incident state in which the detection light 1 is not incident on the photomultiplier tube 2 (step S240). In this case, the PC 4A calculates the signal amount area composed of only dark current pulses.

Next, incidence of the detection light 1 on the photomultiplier tube 2 is started, and data within a fixed period of time is added to calculate the light emission signal amount (step S240). In this case, the start of light emission is synchronized with the start of measurement of the signal amount.

The other configurations are the same as those in the first embodiment.

In the present embodiment configured as above as well, effects similar to those in the first embodiment can be achieved.

Third Embodiment

A third embodiment of the present invention will be described with reference to FIG. 9.

In the present embodiment, the light amount detection device according to the first embodiment is applied to a charged particle beam apparatus.

Figure 9:
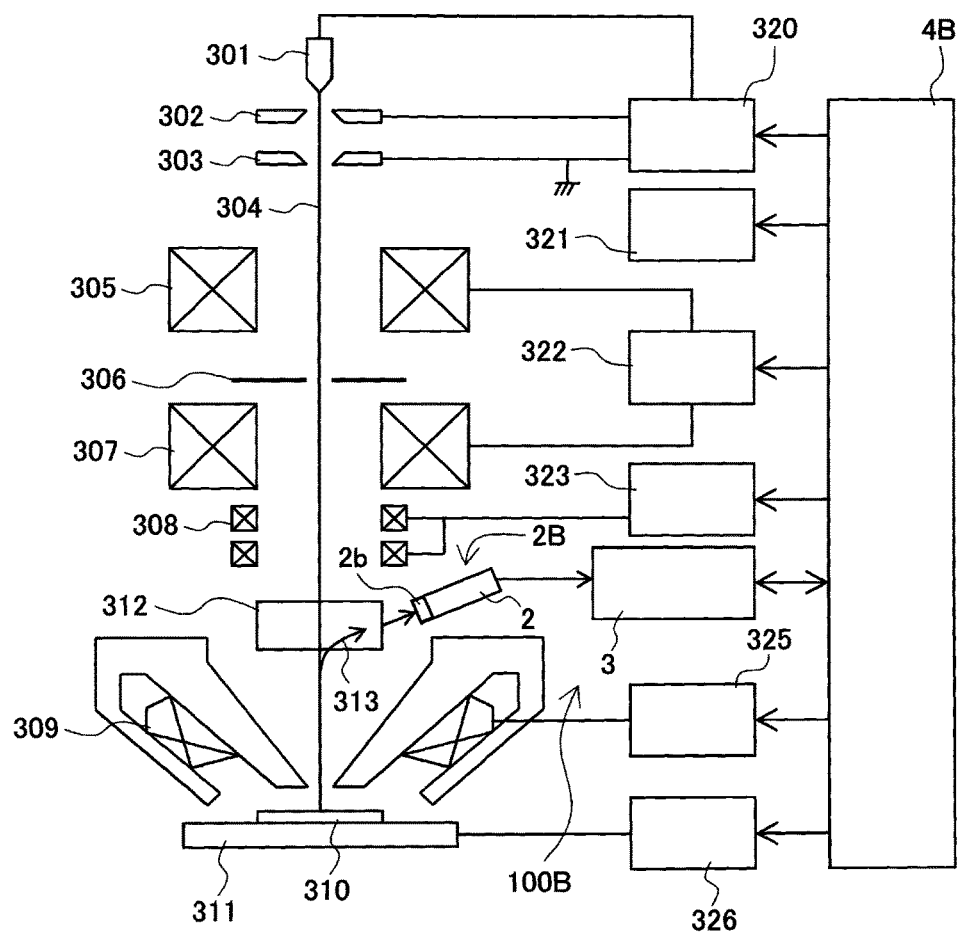
FIG. 9 is a diagram schematically illustrating an overall configuration of a charged particle beam apparatus according to a third embodiment.

FIG. 9 is a diagram schematically illustrating an overall configuration of a charged particle beam apparatus according to the present embodiment. In the figure, the same reference numerals are used to denote members similar to those in the first embodiment, and thus the description thereof will be omitted.

In FIG. 9, a charged particle beam apparatus 300 is schematically configured to include an electron source 301, an extraction electrode 302, an accelerating electrode 303, a first focusing electrode 305, a diaphragm 306, a second focusing electrode 307, an electron beam scanning deflector 308, an objective lens 309, a sample stage 311, an ExB deflector 312, a secondary electron detector 2B, a high-pressure control unit 320, an aligner control unit 321, a focusing lens control unit 322, a deflection control unit 323, a detection circuit 3, an objective lens control unit 325, a stage control unit 326, and a computer 4B.

A sample to be inspected 310 such as a wafer is held on the sample stage 311.

The extraction electrode 302 and the accelerating electrode 303 cause the electron beam 304 to be emitted from the electron source 301. Subsequently, the electron beam 304 is converged by the first focusing electrode 305, the diaphragm 306 and the second focusing electrode 307, and is deflected by the electron beam scanning deflector 308. The electron beam 304 then scans over the sample to be inspected 310 through the objective lens 309.

When the sample to be inspected 310 is irradiated with the electron beam 304, a reflected electron and a secondary electron 313 are generated. The reflected electron and the secondary electron 313 are accelerated by the EXB deflector 312, and are detected by a secondary electron detector 2B.

The detection signal obtained by detecting the reflected electron and the secondary electron 313 by the secondary electron detector 2B is input into a computer 4B through the detection circuit 3. The computer 4B generates image data on the basis of control information. The generated image data is displayed on a display device (not illustrated) as an image.

The electron source 301, the extraction electrode 302 and the accelerating electrode 303 are controlled by the high-pressure control unit 320; the first focusing electrode 305 and the second focusing electrode 307 are controlled by the focusing lens control unit 322; the electron beam scanning deflector 308 is controlled by the deflection control unit 323; the objective lens 309 is controlled by the objective lens control unit 325; and the sample stage 311 is controlled by the stage control unit 326.

In the charged particle beam apparatus 300 configured as above, the secondary electron detector 2B, the detection circuit 3, and a part of the computer 4B constitute a light amount detection device 100B. The secondary electron detector 2B is configured to include: the photomultiplier tube 2; and a scintillator 2b that converts the reflected electron and the secondary electron 213 into light (the detection light 1).

In other words, the light amount detection device 100B according to the present embodiment is schematically configured to include: the photomultiplier tube 2 as a light detection unit that detects light incident from the scintillator 2b to convert the incident light into a current, and outputs the current as a detection signal; the preamplifier 5 as an amplifier that performs amplification processing of amplifying the detection signal from the photomultiplier tube 2; the A/D converter 6 that performs A/D conversion processing of converting the detection signal amplified by the preamplifier 5 into a digital signal to output the digital signal; the base voltage calculation part 9 that performs base voltage calculation processing of, for an output signal from the A/D converter 6, calculating, as a base voltage, a time average value of signal components each having a voltage lower than a predetermined base threshold value; the base threshold value input part 10 that inputs a base threshold value into the base voltage calculation part 9 on the basis of an instruction from the computer 4B; the base correction processing part 8 that performs base correction processing of offsetting an output signal from the A/D converter 6 in such a manner that the base voltage calculated by the base voltage calculation part 9 becomes 0 (zero); the threshold value processing part 11 as a dark current calculation part that performs threshold value processing of, for an output signal from the base correction processing part 8, calculating, as a detection light pulse, a signal component having a voltage higher than a predetermined signal detection threshold value, and dark current calculation processing of, for an output signal from the base correction processing part 8 in a non-incident state in which light is not incident on the photomultiplier tube 2, calculating, as a dark current pulse, a signal component having a voltage higher than a predetermined signal detection threshold value; the signal detection threshold value input part 12 that inputs a signal detection threshold value into the threshold value processing part 11 on the basis of an instruction from the computer 4B; and a part of the computer 4B having a function as a light emission signal amount calculation part that performs light emission signal amount calculation processing of calculating a light emission signal amount by subtracting, from the signal component of the detection light obtained by the threshold value processing, a time average value of the signal components of the dark current obtained by the dark current calculation processing.

The other configurations are the same as those in the first or second embodiment.

In the present embodiment configured as above as well, effects similar to those in the first embodiment can be achieved.

Other Embodiments

The light amount detection device according to the present embodiment can be applied to an immune analyzing apparatus.

As such an immune analyzing apparatus, there is considered, for example, an immune analyzing apparatus, wherein: a measurement cell includes a cell base, a case that houses the photomultiplier tube 2, and a transparent light receiving window that is disposed between the cell base and the case; and a flow channel is formed therebetween, through which a suspension containing a reaction product introduced into the measurement cell flows.

In addition, magnetic particles that do not react with the reaction product are supplemented on a working electrode in the flow channel, and the periphery thereof is filled with a buffer solution containing TPA (tripropylamine) used to induce the excitation of a labeling substance. Subsequently, a voltage based on a determined sequence is applied between the working electrode and counter electrodes that are arranged on both sides thereof on the same plane, thereby causing the labeling substance to induce a luminous reaction.

The photomultiplier tube 2 measures light that is generated by the reaction product in the flow channel, and that passes through a light receiving window plate. The photomultiplier tube 2 is covered by a magnetic sealed tube, and is housed in the case. A socket is mounted to the upper part of the photomultiplier tube 2, and a detection signal of the photomultiplier tube 2 is transmitted to the detection circuit 3 and the PC 4 through this socket, thereby measuring the light intensity.

The other configurations are the same as those in the first or second embodiment.

In the present embodiment configured as above as well, effects similar to those in the first embodiment can be achieved.

It should be noted that the present invention is not limited to the above-described embodiments, and includes various modified examples. For example, the above-described embodiments have been described in detail so as to clearly illustrate the invention of the present application. Therefore, the present invention is not always limited to the invention having all of the disclosed configurations.

REFERENCE SIGNS LIST 1 detection light
2 photomultiplier tube
3 detection circuit
4, 4B computer (PC)
5 preamplifier
6 A/D converter
7 operation part (FPGA)
8 base correction processing part
9 base voltage calculation part
10 base threshold value input part
11 threshold value processing part
12 signal detection threshold value input part
13 detection signal switching unit
100 light amount detection device
300 charged particle beam apparatus

The invention claimed is:
1. A light amount detection device comprising:
an amplifier that performs amplification processing of amplifying a detection signal from a light detection unit for detecting light;
an A/D converter that performs A/D conversion processing of converting the detection signal amplified by the amplifier into a digital signal to output the digital signal;
a base voltage calculation part that performs base voltage calculation processing of, for the output signal from the A/D converter, calculating, as a base voltage, a time average value of signal components each having a voltage lower than a predetermined base threshold value;
a base correction processing part that performs base correction processing of offsetting the output signal from the A/D converter in such a manner that the base voltage calculated by the base voltage calculation part becomes 0;

a dark current calculation part that performs dark current calculation processing of, for an output signal from the base voltage calculation processing part in a non-input state in which light is not input into the light detection unit, calculating, as a dark current pulse, a signal component having a voltage higher than a predetermined signal detection threshold value;

a threshold value processing part that performs threshold value processing of, for the output signal from the base voltage calculation processing part, calculating, as a detection light pulse, a signal component having a voltage higher than a predetermined signal detection threshold value; and a light emission signal amount calculation part that performs light emission signal amount calculation processing of calculating a light emission signal amount by subtracting, from the signal component of the detection light obtained by the threshold value processing, a time average value of the signal components of the dark current obtained by the dark current calculation processing.

2. The light amount detection device according to claim 1, wherein the base voltage calculation processing and the dark current calculation processing are executed in parallel.

3. The light amount detection device according to claim 1, further comprising an output signal storage unit that stores an output signal from the A/D converter, and outputs the output signal as necessary, wherein the dark current calculation processing, the threshold value processing, and the light emission signal amount calculation processing are performed on the basis of the output signal from the output signal storage unit.

4. The light amount detection device according to claim 1, further comprising a detection signal switching unit that switches between presence and absence of an output of a detection signal from the light detection unit.

5. The light amount detection device according to claim 1, wherein the base voltage calculation processing is performed in a non-input state in which light is not input into the light detection unit, or in a state in which no detection signal is output from the light detection unit.

6. An immune analyzing apparatus comprising:

a flow cell into which a mixed solution is introduced, the mixed solution being composed of a sample to be measured, and a reagent containing a light-emitting element and magnetic particles, the reagent being combined with a specific component in the sample to form a complex;

a magnetic field generator that generates a magnetic field for capturing the complex in the mixed solution, which has been introduced into the flow cell, in a predetermined measurement region in the flow cell; and the light amount detection device according to claim 1, the light amount detection device detecting light generated from the complex captured in the measurement region.

7. A charged particle beam apparatus comprising:

a sample stage on which a sample to be measured is arranged;

a charged particle beam irradiation device that irradiates the sample on the sample stage with a charged particle beam; and the light amount detection device according to claim 1, the light amount detection device detecting light generated in a scintillator by a secondary electron that is obtained by irradiating the sample with the charged particle beam.

* * * * *